(12) United States Patent
Cheng

(10) Patent No.: US 11,986,494 B2
(45) Date of Patent: *May 21, 2024

(54) MATERIALS AND METHODS FOR PREVENTION AND TREATMENT OF DIARRHEA AND INFLAMMATION IN THE GASTROINTESTINAL TRACT

(71) Applicant: University of Florida Research Foundation, Inc., Gainesville, FL (US)

(72) Inventor: Sam Xianjun Cheng, Gainesville, FL (US)

(73) Assignee: UNIVERSITY OF FLORIDA RESEARCH FOUNDATION, INC., Gainesville, FL (US)

(*) Notice: Subject to any disclaimer, the term of this patent is extended or adjusted under 35 U.S.C. 154(b) by 639 days.

This patent is subject to a terminal disclaimer.

(21) Appl. No.: 17/120,883

(22) Filed: Dec. 14, 2020

(65) Prior Publication Data

US 2021/0100836 A1  Apr. 8, 2021

Related U.S. Application Data

(63) Continuation of application No. 15/997,352, filed on Jun. 4, 2018, now Pat. No. 10,864,230, which is a continuation of application No. 14/433,996, filed as application No. PCT/US2013/065060 on Oct. 15, 2013, now Pat. No. 9,987,306.

(60) Provisional application No. 61/768,491, filed on Feb. 24, 2013, provisional application No. 61/713,927, filed on Oct. 15, 2012.

(51) Int. Cl.
| | |
|---|---|
| A61K 33/30 | (2006.01) |
| A23L 33/00 | (2016.01) |
| A61K 9/00 | (2006.01) |
| A61K 9/08 | (2006.01) |
| A61K 31/132 | (2006.01) |
| A61K 31/405 | (2006.01) |
| A61K 33/00 | (2006.01) |
| A61K 33/06 | (2006.01) |
| A61K 33/10 | (2006.01) |
| A61K 45/06 | (2006.01) |
| A61P 1/12 | (2006.01) |

(52) U.S. Cl.
CPC ............ *A61K 33/30* (2013.01); *A23L 33/40* (2016.08); *A61K 9/0095* (2013.01); *A61K 9/08* (2013.01); *A61K 31/132* (2013.01); *A61K 31/405* (2013.01); *A61K 33/00* (2013.01); *A61K 33/06* (2013.01); *A61K 33/10* (2013.01); *A61K 45/06* (2013.01); *A61P 1/12* (2018.01); *A23V 2002/00* (2013.01); *Y02A 50/30* (2018.01)

(58) Field of Classification Search
CPC ... A61P 1/12; A61P 1/00; A61K 33/30; A61K 8/27; A61K 31/315; A61K 47/18; A61K 47/183; A61K 9/0095
See application file for complete search history.

(56) References Cited

U.S. PATENT DOCUMENTS

| | | | |
|---|---|---|---|
| 5,922,766 A | 7/1999 | Acosta et al. | |
| 9,987,306 B2* | 6/2018 | Cheng | A61K 33/06 |
| 10,864,230 B2* | 12/2020 | Cheng | A23L 33/40 |
| 2003/0077333 A1 | 4/2003 | Phillips et al. | |
| 2007/0218109 A1 | 9/2007 | Tanaka et al. | |
| 2011/0014167 A1 | 1/2011 | Bindels et al. | |
| 2011/0245171 A1 | 10/2011 | Hardin et al. | |
| 2012/0121562 A1 | 5/2012 | Bergonzelli Degonda et al. | |
| 2013/0196958 A1 | 8/2013 | Harris, Jr. et al. | |
| 2015/0290243 A1 | 10/2015 | Cheng | |
| 2016/0022793 A1 | 1/2016 | Larkin et al. | |

FOREIGN PATENT DOCUMENTS

| | | |
|---|---|---|
| EP | 1197214 A1 | 4/2002 |
| WO | 2009142755 A2 | 11/2009 |

OTHER PUBLICATIONS

Alam, N. H. et al., "Efficacy and safety of oral rehydration solution with reduced osmolarity in adults with cholera: a randomised double-blind clinical trial." The Lancet, Jul. 1999, 354: 296-299.

* cited by examiner

*Primary Examiner* — Robert T. Crow
*Assistant Examiner* — John P Nguyen
(74) *Attorney, Agent, or Firm* — SALIWANCHIK, LLOYD & EISENSCHENK

(57) ABSTRACT

The present invention pertains to the use of the calcium-sensing receptor (CaSR)-activating nutrients (designated as "CaSR-based nutrients") for the prevention and/or treatment of diarrheal diseases and inflammation in the gastrointestinal tract. In one embodiment, the current invention is formulated for oral administration. The anti-diarrheal composition of the present invention is useful for treating diarrheal and gastrointestinal inflammatory conditions in infants and young children.

3 Claims, 19 Drawing Sheets

CaSR-activating nutrient ameliorates DSS-induced colitis

Animal treatment protocol:

Day 0    14    21

Diet + DSS

Diet tested: 1) normal control diet
2) High (2.5x RDA) calcium diet
3) High (2.5x RDA) spermine diet
4) High (2.5x RDA) tryptophan diet All diets were obtained from Altromin, Germany
DSS= dextran sulfate sodium, 3% (w/v) via drinking water

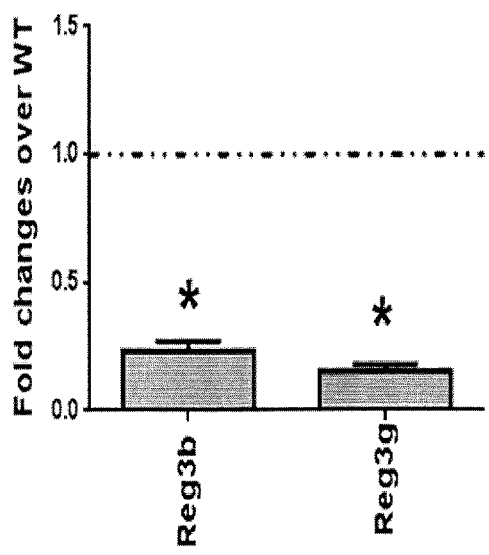
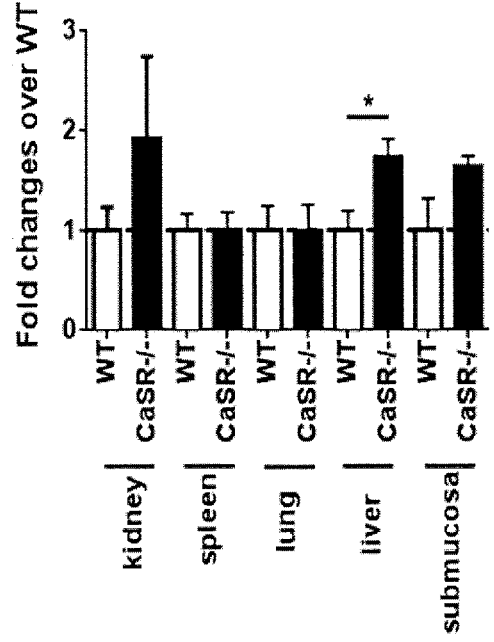
FIG. 8B

Defective CaSR signaling ➔ ↑ activated DCs in MLN and spleen
MLN & Spleen
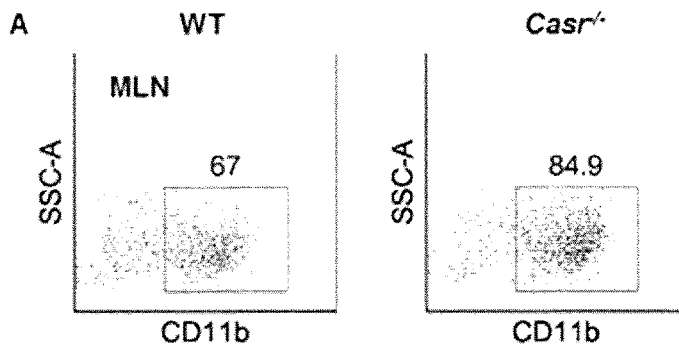
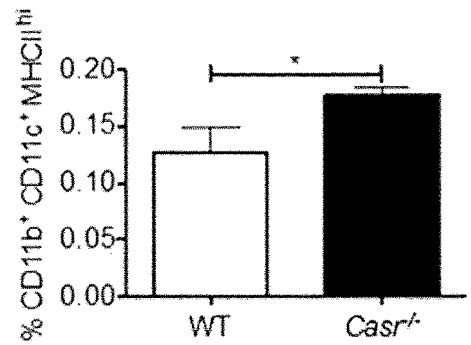
FIG. 11A
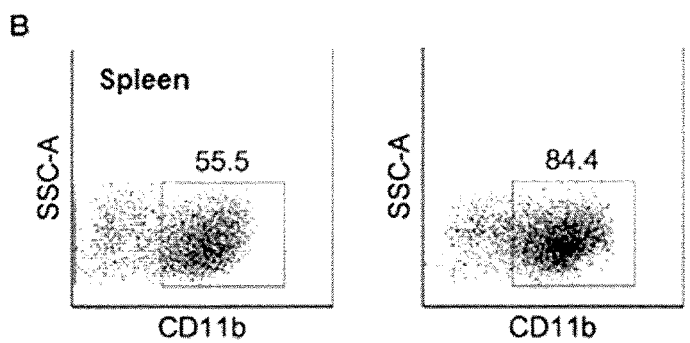
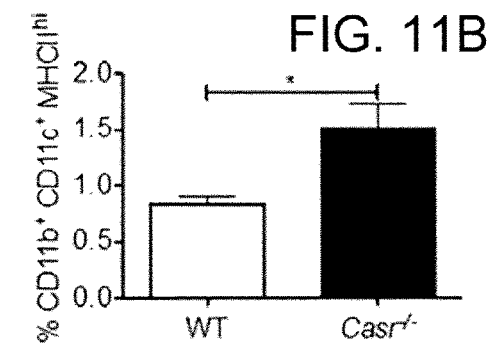
FIG. 11B
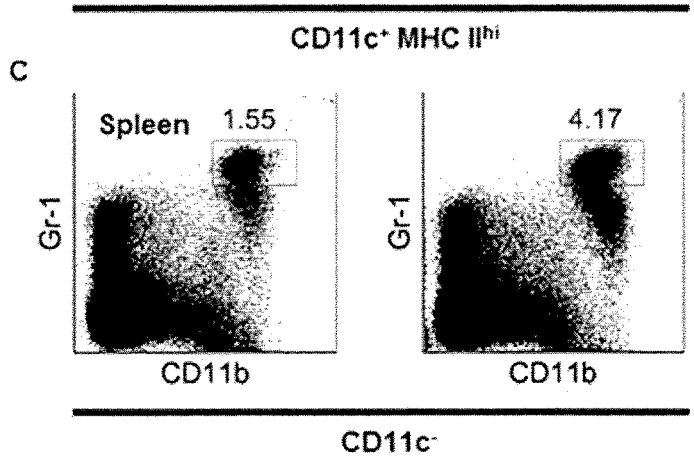
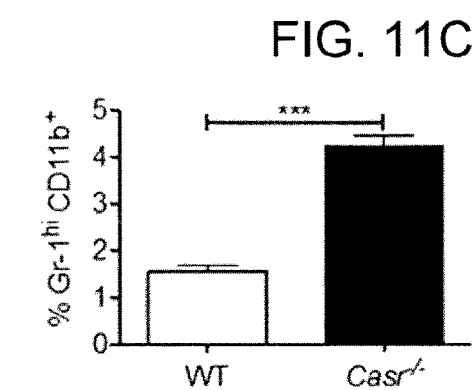
FIG. 11C

Defective CaSR signaling → ↑ activated DCs

Spleen

Defective CaSR signaling ➔ ↑ CD4 & CD8 T cells
MLN & Spleen
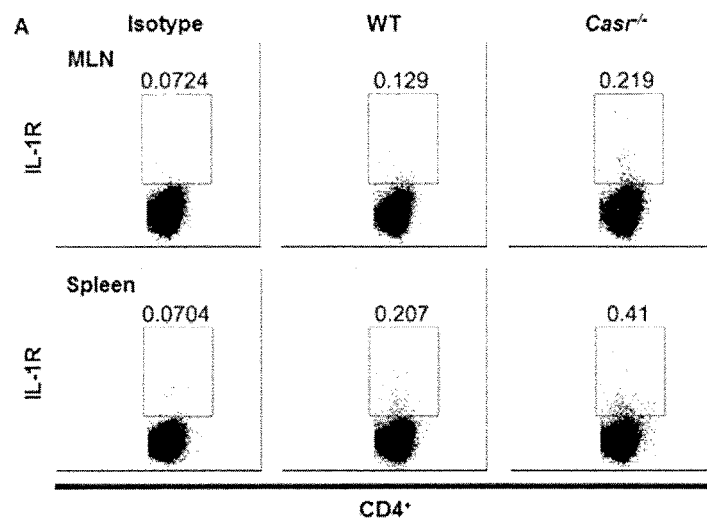
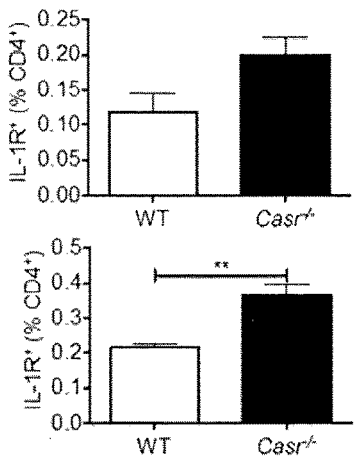
FIG. 14A
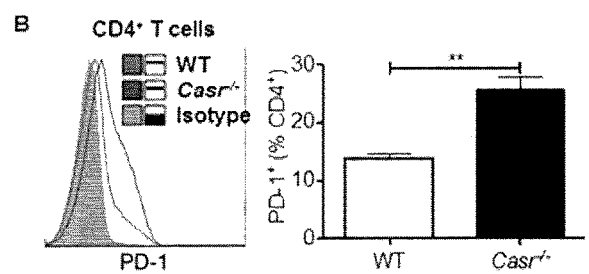
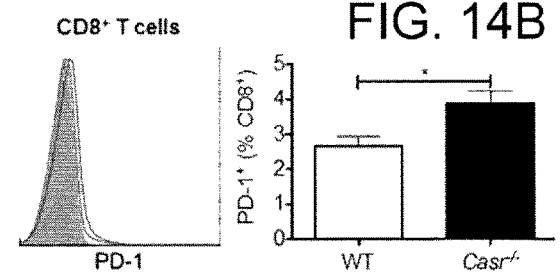
FIG. 14B
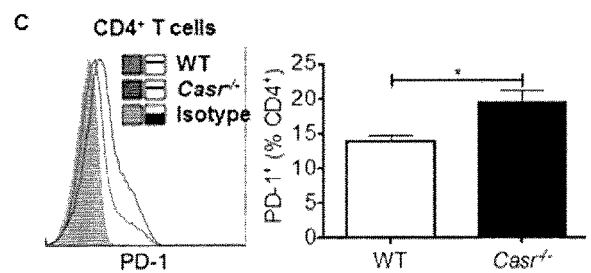
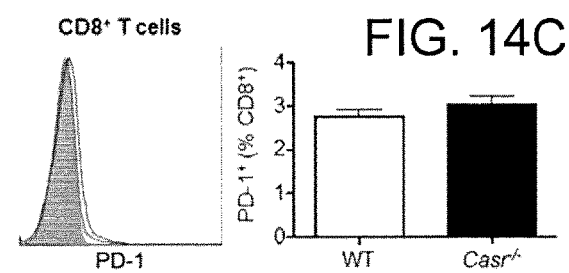
FIG. 14C

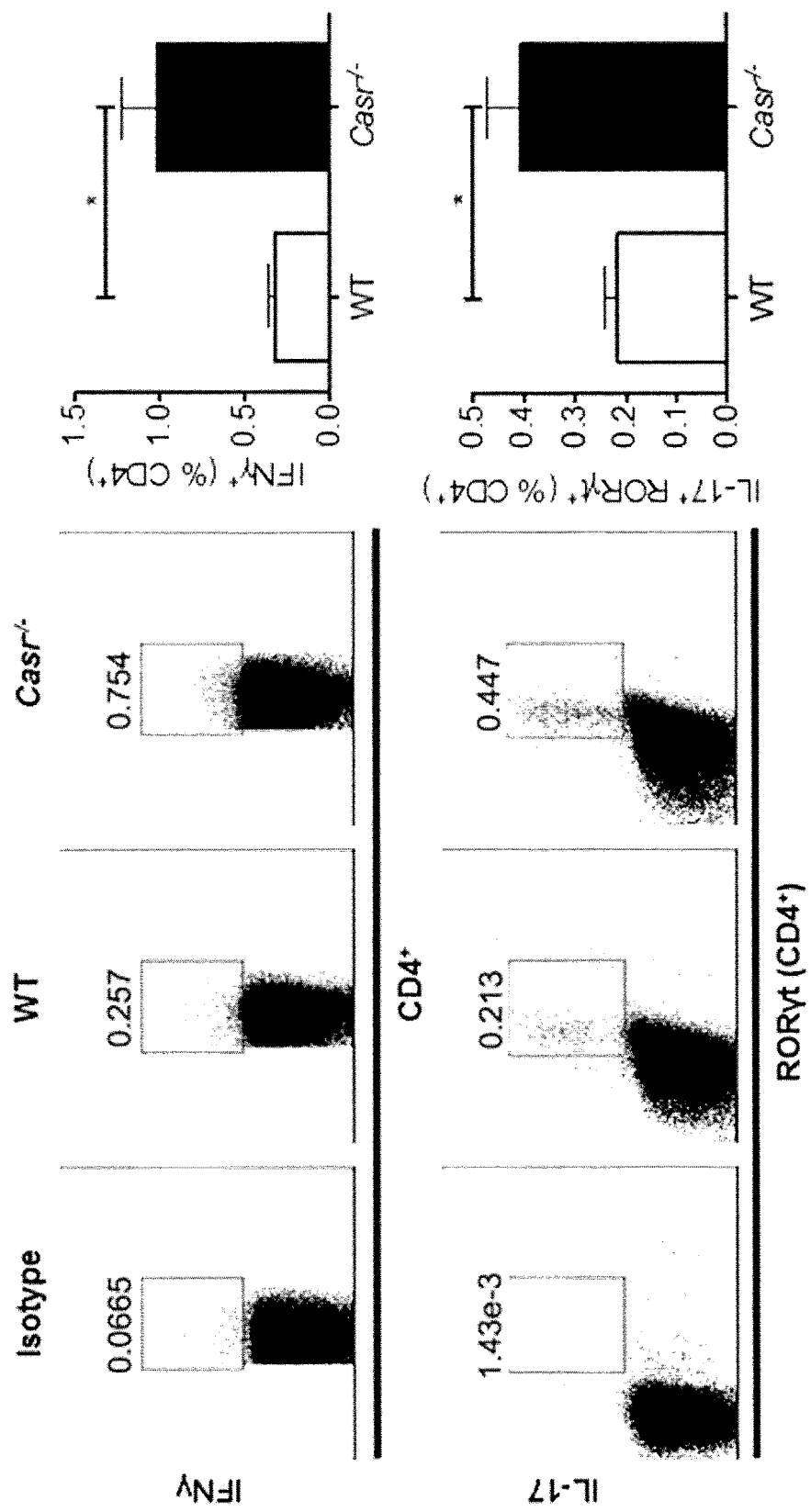
FIG. 15 MLN

MATERIALS AND METHODS FOR PREVENTION AND TREATMENT OF DIARRHEA AND INFLAMMATION IN THE GASTROINTESTINAL TRACT

CROSS REFERENCE TO A RELATED APPLICATION

This application is a continuation of co-pending U.S. application Ser. No. 15/997,352, filed June 4, 2018; which is a continuation of U.S. application Ser. No. 14/433,996, filed Apr. 7, 2015 (now U.S. Pat. No. 9,987,306); which is a U.S. National Stage Application of International Application Number PCT/US2013/065060, filed Oct. 15, 2013; which claims the benefit of U.S. Provisional Application Ser. No. 61/713,927, filed Oct. 15, 2012 and U.S. Provisional Application Ser. No. 61/768,491, filed Feb. 24, 2013, all of which are incorporated herein by reference in their entirety.

BACKGROUND OF INVENTION

Diarrhea is a common illness affecting people of all ages The loss of fluids through diarrhea can cause dehydration and electrolyte disturbances.

In the United Sates, adults have an average of one episode of acute diarrhea each year; diarrhea occurs more frequently in children and infants. Diarrhea is also a common cause of death in developing countries and the second most common cause of infant deaths worldwide.

Acute diarrhea is usually caused by bacterial, viral, or parasitic infections. Chronic diarrhea can be caused by functional disorders such as irritable bowel syndrome or inflammatory diseases such as Crohn's disease.

Oral rehydration solution (ORS), a passive rehydrating solution, is a common treatment for dehydration associated with diarrhea, especially for children with acute diarrhea. The ORS does not alleviate diarrhea or provide treatment for infection or inflammation associated with diarrhea.

Improved formulations for treatment of diarrhea and infection or inflammation in the gastrointestinal tract are needed.

BRIEF SUMMARY

In one embodiment, the present invention pertains to the use of the calcium-sensing receptor (CaSR)-activating nutrients (designated as "CaSR-activating nutrients") for the prevention and/or treatment of diarrheal conditions and/or inflammation in the gastrointestinal tract.

In one embodiment, the current invention is formulated for oral administration. In one embodiment, the anti-diarrheal and/or immune-modulating composition is formulated into an infant formula or adult nutritional composition.

In one embodiment, the present invention provides a composition for preventing or treating diarrhea and/or inflammation in the gastrointestinal tract, wherein the composition comprises, consists essentially of, or consists of, as the active ingredients, one or more ingredients selected from calcium, magnesium, zinc, polyamine(s), aromatic free amino acid(s), short chain (such as C2-C6) fatty acids such as butyrate and propionate, and oligo-peptide(s); and, optionally, therapeutically-acceptable carriers.

In one embodiment, the composition has a pH from about 7.1 to 7.9, preferably, about 7.4-7.6.

In certain embodiments, the composition of the present invention has a molar concentration of 30 mM to 150 mM, or any values therebetween, including but not limited to, 60 mM to 110 mM.

Also provided are methods wherein the composition of the present invention is useful for prevention and/or treatment of diarrhea and/or inflammation in the gastrointestinal tract. The anti-diarrheal and/or immune-modulating composition of the present invention is useful for treating diarrheal diseases and/or inflammation in the gastrointestinal tract in infants and young children.

In one embodiment, the present invention can be used to treat, or prevent the recurrence of, irritable bowel syndrome (IBS). In another embodiment, the present invention can be used to treat, or prevent the recurrence of, inflammatory bowel diseases.

BRIEF DESCRIPTION OF THE DRAWINGS

FIGS. 8A-8B show that CaSR regulates intestinal epithelial barrier.

FIGS. 11A-11C show that defective CaSR signaling increases activated dendritic cells.

FIGS. 14A-14C show that defective CaSR signaling leads to increased CD4 & CD8 T cells.

FIG. 15 shows that defective CaSR signaling leads to increased Th17 T cells.

DETAILED DISCLOSURE

Figure 1:
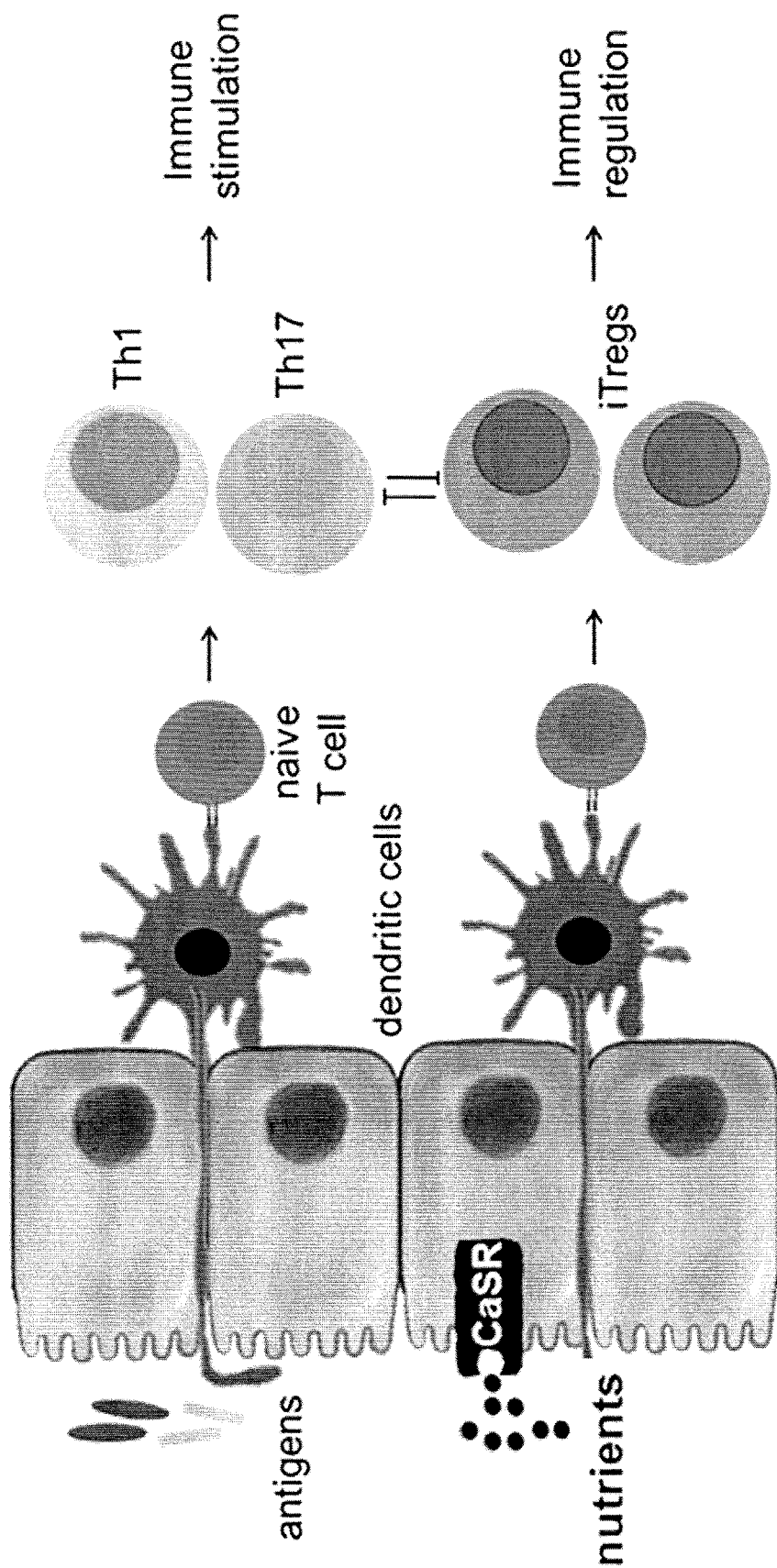
FIG. 1 shows that calcium sensing receptor (CaSR) regulates immune responses in the intestine.

In one embodiment, the present invention pertains to the use of the calcium-sensing receptor (CaSR)-activating nutrients (designated as "CaSR-activating nutrients") for the prevention and/or treatment of diarrheal conditions and/or inflammation in the gastrointestinal tract. In one embodiment, the present invention pertains to the use of CaSR-activating nutrients for treating dehydration, metabolic acidosis, and/or electrolyte disturbances in diarrheal patients. In one embodiment, the current invention is formulated for oral administration.

CaSR-activating nutrients of the present invention can be used to treat metabolic acidosis by modulating the exaggerated intestinal bicarbonate secretion in various forms of diarrhea. Advantageously, the anti-diarrheal composition of the present invention is useful for treating diarrheal conditions in infants and young children.

In one embodiment, the present invention provides a composition for preventing or treating diarrhea, wherein the composition comprises, consists essentially of, or consists of, as the active ingredients, one or more ingredients selected from calcium, magnesium, zinc, polyamine(s), aromatic free amino acid(s), short chain (such as C2-C6) fatty acids such as butyrate and propionate, and oligo-peptide(s); and, optionally, therapeutically-acceptable carriers.

In certain embodiments, the present invention provides a composition for preventing or treating diarrhea, wherein the composition comprises, consists essentially of, or consists of, as the active ingredients, at least one, at least two, at least three, at least four, at least five, at least six, at least seven, at least eight, at least nine, at least ten, at least eleven, at least twelve ingredients selected from calcium, magnesium, zinc, polyamine(s), aromatic free amino acid(s), short chain (such as C2-C6) fatty acids such as butyrate and propionate, and oligo-peptide(s); and, optionally, therapeutically-acceptable carriers.

In certain embodiments, the CaSR nutrient-based anti-diarrheal composition modulates the activity, tone, and/or responsiveness of the enteric nervous system; is pro-absorptive and anti-diarrheal; is anti-inflammatory; and/or has positive benefits toward bone health, overall nutrition, and growth.

The CaSR nutrient-based anti-diarrheal composition potently modulates the activity of the enteric nervous system. In one embodiment, the nutrient-based anti-diarrheal composition is orally administered for a long period of time (such as, for example, for a period of more than 10 days, or any time period longer than 10 days including, but not limited to, more than 15 days; more than 1, 2, 3, 4, 5, 6, 7, 8, 9, 10, 11, or 12 months) to modulate the tone and responsiveness of the enteric nervous system.

The CaSR nutrient-based oral anti-diarrheal composition not only promotes rehydration, but also arrests fluid loss from the gut and promotes gut healing.

Also provided are methods wherein the composition of the present invention is useful for prevention and/or treatment of diarrhea and/or inflammation in the gastrointestinal tract.

Anti-Diarrheal and Immune-Modulating Compositions

In one embodiment, the present invention provides a composition for preventing and/or treating diarrhea and/or inflammation. In one embodiment, the composition comprises, consists essentially of, or consists of, one or more CaSR-activating compounds.

As used herein, "calcium sensing receptor (CaSR)" refers to the G-protein-coupled receptor responding to changes in extracellular calcium and/or magnesium levels. Activation of the CaSR produces rapid, transient increases in cytosolic calcium concentration by mobilizing calcium from thapsigargin-sensitive intracellular stores and by increasing calcium influx though voltage-insensitive calcium channels in the cell membrane (Brown et al., Nature 366: 575-580, 1993; Yamaguchi et al., Adv Pharmacol 47: 209-253, 2000).

In one embodiment, the CaSR-activating compound is a CaSR agonist (such as cinacelcet). In one embodiment, the CaSR-activating compound is a natural compound. In one embodiment, the CaSR-activating compound is a non-natural compound. In one embodiment, the CaSR-activating compound is a synthetic compound.

The term "natural compound," as used herein, refers to a compound or substance that exists in nature.

The term "non-natural compound," as used herein, refers to a compound or substance that does not exist in nature.

In certain embodiments, CaSR activating compounds useful according to the present invention include, but are not limited to, calcium, magnesium, zinc, polyamine(s), aromatic free amino acid(s), short chain (such as C2-C6) fatty acids such as butyrate and propionate, and oligo-peptide(s).

In certain embodiments, CaSR activating compounds useful according to the present invention include synthetic, non-natural CaSR-agonists, such as synthetic, non-natural calcimimetic compounds described in U.S. Patent Application Publication No. 20070060625, which is hereby incorporated by reference in its entirety.

In one embodiment, the present invention provides a composition for preventing and/or treating diarrhea and/or inflammation in the gastrointestinal tract, wherein the composition comprises, consists essentially of, or consists of, one or more ingredients selected from calcium, magnesium, zinc, polyamine(s), aromatic free amino acid(s), short chain (such as C2-C6) fatty acids such as butyrate and propionate, and oligo-peptide(s); and, optionally, an "oral rehydration solution" or PEDIALYTE® compositions; antibiotics including, but not limited to, amoxacillin, augmentin, metronidazole, and clindamycin; one or more anti-inflammatory agents including, but not limited to, anti-inflammatory steroid drugs such as glucocorticoids, and 5-aminosalicylic acid (5-ASA); probiotics; and/or therapeutically-acceptable carriers.

In one embodiment, the composition is formulated into an infant formula, for administration to infants and/or children of 5 years old or younger.

The term "infant," as used herein, refers to a human subject of less than 1 year of age.

In one embodiment, the composition further comprises a PEDIALYTE® formulation. PEDIALYTE® is sterilized oral glucose electrolyte solutions intended for the management of dehydration due to diarrhea. Salts and electrolytes in PEDIALYTE® replace fluid and electrolyte losses in diarrhea. In one embodiment, the PEDIALYTE® formulation consists of the following ingredients: sodium chloride (1.75 gm); trisodium citrate dihydrate (1.45 gm); potassium chloride (0.75 gm); glucose anhydrous (10.0 gm); and a carrier.

In one embodiment, the composition comprises one or more agents selected from sodium chloride, trisodium citrate dehydrate, potassium chloride, and glucose anhydrous.

In one embodiment, the oral rehydration composition comprises sodium, potassium, chloride, bicarbonate, citrate and glucose.

In one embodiment, the present invention provides a composition for preventing or treating diarrhea and/or inflammation in the gastrointestinal tract, wherein the composition comprises, consists essentially of, or consists of, calcium, magnesium, zinc, polyamine(s), aromatic free amino acid(s), short chain (C2-C6) fatty acids such as butyrate and propionate, and oligo-peptide(s); and optionally, therapeutically-acceptable carriers.

In one embodiment, the anti-diarrheal composition comprises, consists of, or consists essentially of, potassium (15-25 mEq/L), sodium (45-50 mEq/L), chloride (30-40 mEq/L), calcium (3-6 mM), magnesium (2-4 mM), $HCO_3^-$ (25-35 mM), zinc (2-5 mM) or zinc sulfate (10-20 mg/L), tryptophan (7-15 mM), and spermine (0.1-2mM); and optionally, therapeutically-acceptable carriers.

In one embodiment, the composition has a pH from about 7.0 to about 8.0 or any pH values therebetween, including, but not limited to, 7.1 to 7.9, and 7.4 to 7.6.

Also, a low ionic strength of the composition increases CaSR activity. In certain embodiments, the composition of the present invention has a molar concentration that is lower than traditional oral rehydration solutions. In certain embodiments, the composition of the present invention has a molar concentration of less than 150 mM, or any values lower than 150 mM, including but not limited to, lower than 140 mM, lower than 130 mM, lower than 120 mM, lower 110 mM, lower than 100 mM, lower than 90 mM, lower than 80 mM, lower than 70 mM, lower than 60 mM, lower than 50 mM.

In certain embodiments, the composition of the present invention has a molar concentration of 30 mM to 150 mM, or any values therebetween, including but not limited to, 50 mM to 130 mM, 60 mM to 110 mM, 65 rnM to 100 mM, and 70 mM to 95 mM.

In certain embodiments, the total osmolarity of the composition is from about 150 mosm to 260 mosm, or any value therebetween, including but not limited to, 180 mosm to 250 mosm, and 200 mosm to 220 mosm.

In certain embodiments, the total osmolarity of the composition is lower than 260 mosm, or any value lower than 260 mosm, including but not limited to, 250 mosm, 220 mosm, and 200 mosm.

In certain embodiments, the composition comprises $HCO_3^-$ and/or $CO_3^{2-}$; and phosphate ions, such as $H_2PO_4^-$, $HFO_4^{2-}$, and $PO_4^{3-}$.

The term "consisting essentially of," as used herein, limits the scope of the ingredients and steps to the specified materials or steps and those that do not materially affect the basic and novel characteristic(s) of the present invention, i.e., compositions and methods for prevention and/or treatment of diarrhea and/or inflammation in the gastrointestinal tract. By using the term "consisting essentially of," the composition may comprise substances that do not have therapeutic effects on the treatment of diarrhea and/or inflammation in the gastrointestinal tract; such ingredients include carriers, excipients, adjuvants, preservatives, flavoring agents, etc that do not have an effect for prevention and/or treatment of diarrhea and/or inflammation in the gastrointestinal tract.

Aromatic free amino acids useful for the prevention and/or treatment of diarrhea and/or inflammation in the gastrointestinal tract include, but are not limited to, phenylalanine, tyrosine, and tryptophan.

Polyamine compounds useful for the prevention and/or treatment of diarrhea and/or inflammation in the gastrointestinal tract include, but are not limited to, spermine, spermidine, ornithine, and putrescine. The term "oligopeptide," as used herein, refers to a peptide consisting of three to twenty amino acids.

The term "oligosaccharides," as used herein, refers to a saccharide consisting of three to twenty monosaccharides.

Short chain fatty acids are fatty acids with aliphatic tails of two to six carbons, and include, but are not limited to, formic acid, acetic acid, propionic acid, isobutyric acid (2-methylpropanoic acid), butyric acid, isovaleric acid (3-methylbutanoic acid), and valeric acid (pentanoic acid).

In one embodiment, the composition comprises carbohydrates including, monosaccharides (such as glucose), disaccharides, oligosaccharides, and/or polysaccharides. In one embodiment, the composition comprises dextrose and/or amylase-resistant starch. In another embodiment, the composition of the present invention does not contain carbohydrates. In another embodiment, the composition of the present invention does not contain glucose.

In one embodiment, the composition comprises one or more free amino acids selected from alanine, asparagine, aspartic acid, cysteine, glutamic acid, phenylalanine, glycine, histidine, isoleucine, lysine, leucine, methionine, proline, glutamine, arginine, serine, threonine, valine, tryptophan, and tyrosine; and/or dipeptides and/or tripeptides formed from these free amino acids.

In one embodiment, the composition for prevention and/or treatment of diarrhea and/or inflammation in the gastrointestinal tract of the present invention does not encompass one or more, or any of, the calcimimetic compounds described in U.S. Patent Application Publication No. 20070060625.

Prevention and/or Treatment of Diarrhea and Inflammation in the Gastrointestinal Tract In another embodiment, the present invention provides a method for preventing, treating, or ameliorating diarrhea and/or inflammation (such as inflammation in the gastrointestinal tract), wherein the method comprises administering to a patient or subject in need of such prevention or treatment, an effective amount of a composition of the invention.

In one embodiment, the composition comprises, consists essentially of, or consists of, one or more CaSR-activating compounds. In one specific embodiment, the composition comprises, consists essentially of, or consists of, one or more ingredients selected from calcium, magnesium, zinc, polyamine(s), aromatic free amino acid(s), short chain (such as C2-C6) fatty acids such as butyrate and propionate, and oligo-peptide(s); and, optionally, an "oral rehydration solution" or PEDIALYTE® compositions; antibiotics including, but not limited to, amoxacillin, augmentin, metronidazole, and clindamycin; one or more anti-inflammatory agents including, but not limited to, anti-inflammatory steroid drugs such as glucocorticoids, and 5-aminosalicylic acid (5-ASA); probiotics; and/or therapeutically-acceptable carriers.

In a preferred embodiment, the composition is administered via the oral route.

The term "subject" or "patient," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; domesticated animals such as dogs, and cats; livestock such as horses, cattle, pigs, sheep, goats, and chickens; and other animals such as mice, rats, guinea pigs, and hamsters.

In one embodiment, a subject in need of treatment is a patient or subject who has diarrhea.

In another embodiment, a subject in need of treatment is a patient or subject who has inflammation in the gastrointestinal tract (such as the large and small intestine). In one embodiment, a subject in need of treatment is a patient or subject who has an inflammatory disease or disorder in the gastrointestinal tract, such as, an inflammatory bowel disease, such as Crohn's disease and colitis (such as ulcerative colitis).

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, or affecting the progression, severity, and/or scope of a disease or condition.

The term "amelioration" or any grammatical variation thereof (e.g., ameliorate, ameliorating, and amelioration etc.), as used herein, includes, but is not limited to, delaying the onset, or reducing the severity of a disease or condition (e.g., diarrhea), and accelerating recovery from diarrheal diseases.

The term "prevention" or any grammatical variation thereof (e.g., prevent, preventing, and prevention etc.), as used herein, includes but is not limited to, delaying the onset of symptoms, preventing relapse to a disease, increasing latency between symptomatic episodes, or a combination thereof.

The term "treatment," "amelioration," or "prevention," as used herein, does not require the complete absence of symptoms.

The term "effective amount," as used herein, refers to an amount that is capable of treating, preventing, or ameliorating a disease or condition or otherwise capable of producing an intended therapeutic effect.

As used herein, the term "diarrhea" refers to a condition of three or more unformed stools in a 24-hour period of volume more than 200 g per day in adults.

The present invention can be used to treat diarrhea in infants and children; diarrhea in immune compromised or non-compromised patients; acute diarrhea; chronic diarrhea, diarrhea caused by infections, functional disorders, and/or gastrointestinal inflammatory diseases such as inflammatory bowel disease.

In certain embodiments, the present invention can be used to prevent or treat diarrheal conditions including infectious diarrhea caused by viruses, bacteria and parasites; inflammatory diarrhea, such as caused by inflammatory bowel disease and other bowel inflammatory disorders; neurogenic diarrhea, such as caused by with irritable bowel syndrome (IBS); and allergenic diarrhea, such as caused by food allergy and food sensitivity.

In one embodiment, the present invention can be used to treat or prevent inflammation in the gastrointestinal tract (such as the large and small intestine). In one embodiment, the present invention can be used to treat, or prevent the recurrence of, irritable bowel syndrome (IBS). In another embodiment, the present invention can be used to treat, or prevent the recurrence of, inflammatory bowel diseases, including Crohn's disease and colitis (such as ulcerative colitis).

In certain embodiments, the present invention can be used to prevent and/or treat osmotic diarrhea, i.e., if the osmotic pressure of intestinal contents is higher than that of the serum. Osmotic diarrhea may result from malabsorption of fat (e.g., in celiac disease) or of lactose (e.g., in intestinal lactase deficiency), or it can happen due to the use of certain laxatives (e.g., lactulose, magnesium hydroxide) or artificial sweeteners (e.g., sorbitol, mannitol).

In certain embodiments, the present invention can be used to prevent and/or treat secretory diarrhea, i.e., occurring when there is a net secretion of water into the lumen. This may be caused by bacterial toxins (such as those produced, e.g., by *E. coli* and *Vibrio cholerae*).

In certain embodiments, the present invention can be used to prevent and/or treat osmotic and secretory diarrheas resulting from abnormalities in the small intestine such that the flow of water through the ileocecal area overcomes the absorptive capacity of the colon.

In one embodiment, the present invention can be used to prevent and/or treat enteric nervous system (ENS)-mediated diarrheal conditions. In certain embodiments, the present invention can be used to prevent and/or treat exudative diarrhea, i.e., resulting from direct damage to the small or large intestinal mucosa. This type of diarrhea can be caused by infectious or inflammatory disorders of the gut.

In certain embodiments, the present invention can be used to prevent and/or treat exudative diarrhea associated with chemotherapy, radiation treatment, inflammation or toxic traumatic injury, and gastrointestinal or abdominal surgery.

In certain embodiments, the present invention can be used to prevent and/or treat acute diarrhea, chronic diarrhea, and traveler's diarrhea.

As used herein, the term "acute diarrhea" refers to a condition characterized by stool weight more than 200 g/day (in adults) for less than 14 days duration, usually associated with an increased frequency of bowel movements.

Common causes of acute diarrhea include drugs and chemical agents, including laxatives, antacids, antibiotics, cholinergic drugs, lactose, uanethidine, quinidine, digitalis, and colchicine; infections by bacteria such as, *Escherichia coli, Vibrio cholerae, Vibrio parahaemolyticus, Clostridium perfringens, Clostridium difficile, Staphylococcus aureus*, and *Bacteria Salmonella*; infections by viruses such as Parvovirus, Reovirus (rotavirus), Adenovirus, Calicivirus, and Astrovirus; infections by protozoa such as Cryptosporidia, *Giardia lamblia*, and *Entamoeba histolytica*.

As used herein, the term "traveler's diarrhea" refers to a syndrome characterized by an increase in frequency of unformed bowel movements, typically, four to five loose stools per day, with associated symptoms including abdominal cramps, nausea, bloating, urgency, fever and malaise. Traveler's diarrhea can be characterized by an abrupt beginning, during travel or soon after returning home.

As used herein, the term "chronic diarrhea" refers to a condition characterized by stool weight more than 200 g/day (in adults) for more than 14 days duration, usually associated with an increased frequency of bowel movements.

In one embodiment, the composition of the present invention can be administered before, during, or after, the administration of an oral rehydration therapy.

In addition, the composition of the present invention can be administered in conjunction with surgical and non-surgical treatments.

In one embodiment, the composition of the present invention is administered to treat acute diarrheal diseases. In another embodiment, the composition of the present invention provides long-term administration of the anti-diarrheal composition, such as, for a period more than 10 days, or any period of time longer than 10 days, including, but not limited to, more than 15 days, 20 days, 1 month, 2 months, 3 months, 4 months, 5 months, 6 months, 7 months, 8 months, 9 months, 10 months, 11 months, 1 year, 1.5 years, 2 years, 3 years, etc.

In certain embodiments, the composition of the present invention is administered once a day or more than once a day, such as, twice or three times a day. In certain embodiments, the composition of the present invention is administered once a week, or more than once a week, such as twice, three times, four times, five times a week, etc.

Formulations and Administration

The subject invention provides for therapeutic or pharmaceutical compositions comprising a therapeutically effective amount of the subject composition and, optionally, a pharmaceutically acceptable carrier. Such pharmaceutical carriers can be sterile liquids, such as water. The therapeutic composition can also comprise excipients, adjuvants, flavoring agents, etc. In an embodiment, the therapeutic composition and all ingredients contained therein are sterile.

In one embodiment, the composition of the present invention is formulated into an infant formula, for administration to infants and/or children of 5 years old or younger.

In one specific embodiment, the composition of the present invention is formulated into an infant formula or adult nutritional composition. In one embodiment, the infant formula or adult nutritional composition can be milk-based, soy-based, or based on other food sources. In certain embodiments, the composition of the present invention is prepared as a powder or liquid nutritional composition for infant, pediatric and/or adult populations.

In one embodiment, the composition of the present invention is formulated into a nutritionally complete diet by including vitamins and minerals at acceptable levels. The composition of the present invention can be in the form of a dietary product such as an infant formula, milk substitute, or meal replacement or supplement.

In one embodiment, the composition of the present invention is formulated into a nutritionally complete infant formula. The term "nutritionally complete," as used herein, means that the composition contains adequate nutrients to sustain healthy human life for extended periods. In one embodiment, the infant formula of the invention contains ingredients that are designed to meet the nutritional needs of the human infant namely, protein and/or other nutrients such as vitamins and minerals.

Examples of minerals, vitamins and other nutrients optionally present in the composition of the present invention include vitamin A, vitamin $B_6$, vitamin $B_{12}$, vitamin E, vitamin K, vitamin C, folic acid, thiamine, inositol, riboflavin, niacin, biotin, pantothenic acid, choline, calcium, phosphorus, iodine, iron, magnesium, copper, zinc, manganese, chloride, potassium, sodium, selenium, chromium, molybdenum, taurine, and L-carnitine. Minerals can be added in salt forms. In addition to compatibility and stability considerations, the presence and amounts of specific minerals and other vitamins will vary depending on the intended infant population.

In one embodiment, the infant formula of the present invention comprises emulsifiers and stabilizers, including, but not limited to, soy lecithin, carrageenan, and the like.

In certain embodiments, the composition of the present invention is in concentrate liquid form, liquid ready to consume form, or powder form. In one embodiment, the composition of the present invention is in a powder form for combination with a specified amount of water. The composition of the present invention can be sterilized, if desired, by techniques known in the art, for example, heat treatment such as autoclaving or retorting, and the like. The composition of the present invention can be packaged in any type of container known in the art to be used for storing nutritional products such as glass, lined paperboard, plastic, coated metal cans and the like. In one embodiment, the present invention provides a package comprising the composition of the present invention.

In one embodiment, the composition of the present invention is shelf stable after reconstitution. By "shelf stable" is meant that the composition in a form ready to consume remains in a single homogenous phase (i.e., does not separate into more than one phase upon visual inspection) or that the thickener does not settle out as a sediment upon visual inspection after storage overnight in the refrigerator.

The term "carrier" refers to a diluent, adjuvant, excipient, or vehicle with which the compound is administered. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the enteral mode of administration.

The compounds and compositions of the subject invention can be administered to the subject being treated by standard routes, including oral, parenteral administration including intravenous, subcutaneous, intramuscular injection.

The invention also provides a pharmaceutical pack or kit comprising one or more containers filled with one or more of the ingredients, e.g., compound, carrier, or the pharmaceutical compositions of the invention.

EXAMPLES

Following are examples that illustrate procedures and embodiments for practicing the invention. The examples should not be construed as limiting.

Example 1

Formulations for Prevention and/or Treatment of Diarrhea and/or Inflammation in the Gastrointestinal Tract This Example provides embodiments of the anti-diarrheal and immune-modulating composition.
Formulation 1: Anti-Diarrheal and Immune-Modulating Composition Comprising CaSR-Based Nutrients and "Oral Rehydration Solution" or "PEDIALYTE™" Solutions PEDIALYTE™ contains water, Dextrose. Less than 0.5% of: Citric Acid, Potassium Citrate, Salt, Natural & Artificial Flavors, Sodium Citrate, Sucralose, Acesulfame Potassium, Zinc Gluconate, Red 40, and Blue 1.

In one embodiment, the antidiarrheal and immune-modulating composition comprises one or more CaSR-based nutrients selected from calcium, magnesium, zinc, polyamine(s), aromatic free amino acid(s), and oligo-peptide(s); and, optionally, an "oral rehydration solution" or PEDIALYTE® composition.

Advantageously, Formulation 1 not only promotes rehydration, but can also arrest the fluid loss from the gut and promote gut healing, and thus, is useful for treatment of diarrheal and gastrointestinal inflammatory diseases in infants and young children.
Formulation 2: Anti-Diarrheal and Immune-Modulating Composition Comprising CaSR-Based Nutrients And Antibiotics In one embodiment, the present invention provides a composition for preventing and/or treating diarrhea and/or inflammation in the gastrointestinal tract, wherein the composition comprises one or more CaSR-based nutrients selected from calcium, magnesium, zinc, polyamine(s), aromatic free amino acid(s), short chain (such as C2-C6) fatty acids such as butyrate and propionate, and oligo-peptide(s); and, optionally, antibiotics such as, amoxacillin, augmentin, metronidazole, and clindamycin.

Advantageously, Formulation 2 has antibiotic, anti-inflammatory, and anti-diarrheal effects, and thus, can be used to prevent diarrheal events while treating infections. Formulation 2 can provide treatment for diarrheal and/or inflammatory symptoms in patients with infections, which often occur in patients with compromised immune system (such as HIV and other immune deficient patients) as well as in immune-competent patients.

Formulation 3: Anti-Diarrheal and Immune-Modulating Composition Comprising CaSR-Based Nutrients and Anti-Inflammatory Agents In one embodiment, the present invention provides a composition for preventing and/or treating diarrhea and/or inflammation in the gastrointestinal tract, wherein the composition comprises one or more CaSR-based nutrients selected from calcium, magnesium, zinc, polyamine(s), aromatic free amino acid(s), and oligo-peptide(s); and, optionally, one or more anti-inflammatory agents including, but not limited to, anti-inflammatory steroid drugs such as glucocorticoids, and 5-aminosalicylic acid (5-ASA).

Advantageously, Formulation 3 has enhanced anti-inflammatory property, provides nutrition, and has bone health-promoting effect. In one embodiment, Formulation 3 can be used to prevent or treat the osteopenia/osteoporosis associated with the long term use of steroids. In another embodiment, Formulation 3 can be used to treat diarrheal diseases in patients with inflammatory bowel disease.

Formulation 4: Anti-Diarrheal Composition Comprising CaSR-Based Nutrients and Probiotics In one embodiment, the present invention provides a composition for preventing and/or treating diarrhea and/or inflammation in the gastrointestinal tract, wherein the composition comprises one or more CaSR-based nutrients selected from calcium, magnesium, zinc, polyamine(s), aromatic free amino acid(s), and oligo-peptide(s); and, optionally, probiotics.

Formulation 4 has advantageous synergistic effects in promoting intestinal health, when compared to the use of the CaSR nutrients or probiotics alone. Formulation 4 can be used to promote intestinal health both in the general population (without the intestinal diseases) and in patients with gastrointestinal disorders (such as patients with inflammatory bowel disease, infectious diarrhea, or irritable bowel syndrome).

Formulation 5—CaSR Nutrient-Based Antidiarrheal Oral Solution for Children with Diarrheal Diseases Formulation 5
Serving size 1 bottle (237 ml, 8 oz)
Amount per serving

| | |
|---|---|
| Calorie | 24 |
| Potassium | 185 mg |
| Sodium | 245 mg |
| Chloride | 294 mg |
| Calcium | 47 mg |
| Magnesium | 17 mg |
| Bicarbonate | 433 mg |
| Zinc | 2.4 mg |
| Tryptophan | 483 mg |
| Spermine | 48 mg |
| Carbohydrate | 5.91 gram |
| pH | 7.5 |

In one embodiment, the daily dosage for Formulation 5 is 50-150 ml/kg/day.

Example 2

Prevention and Treatment of Inflammation in the Gastrointestinal Tract

This Example shows that CaSR-activating nutrients can be used to modulate gastrointestinal immune responses and reduce inflammation in the gastrointestinal tract (FIG. 1).

Figure 2:
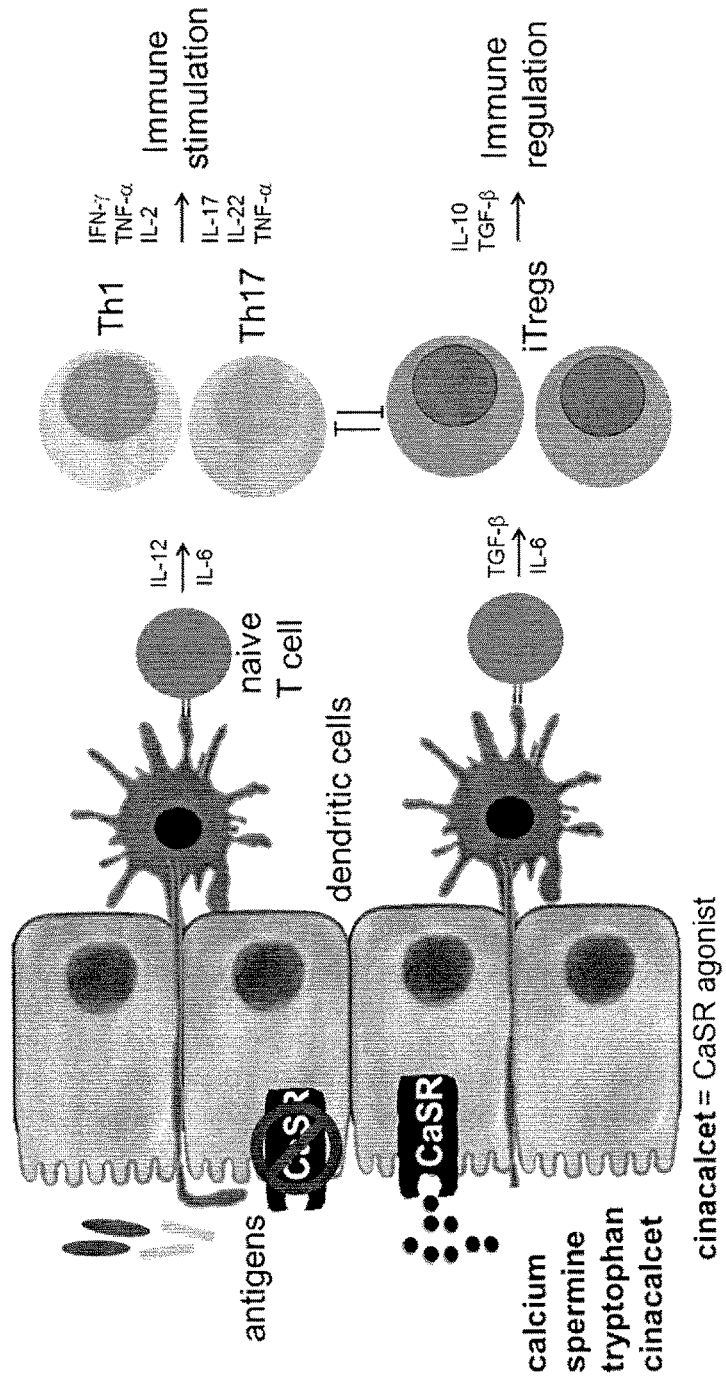
FIG. 2 shows materials and methods used in an experiment showing that CaSR-activating compounds can be used to modulate intestinal immunity and to treat inflammatory diseases in the gastrointestinal tract.
Figure 3:
FIG. 3 shows that CaSR-activating nutrients ameliorate colitis in mice.
Figure 4:
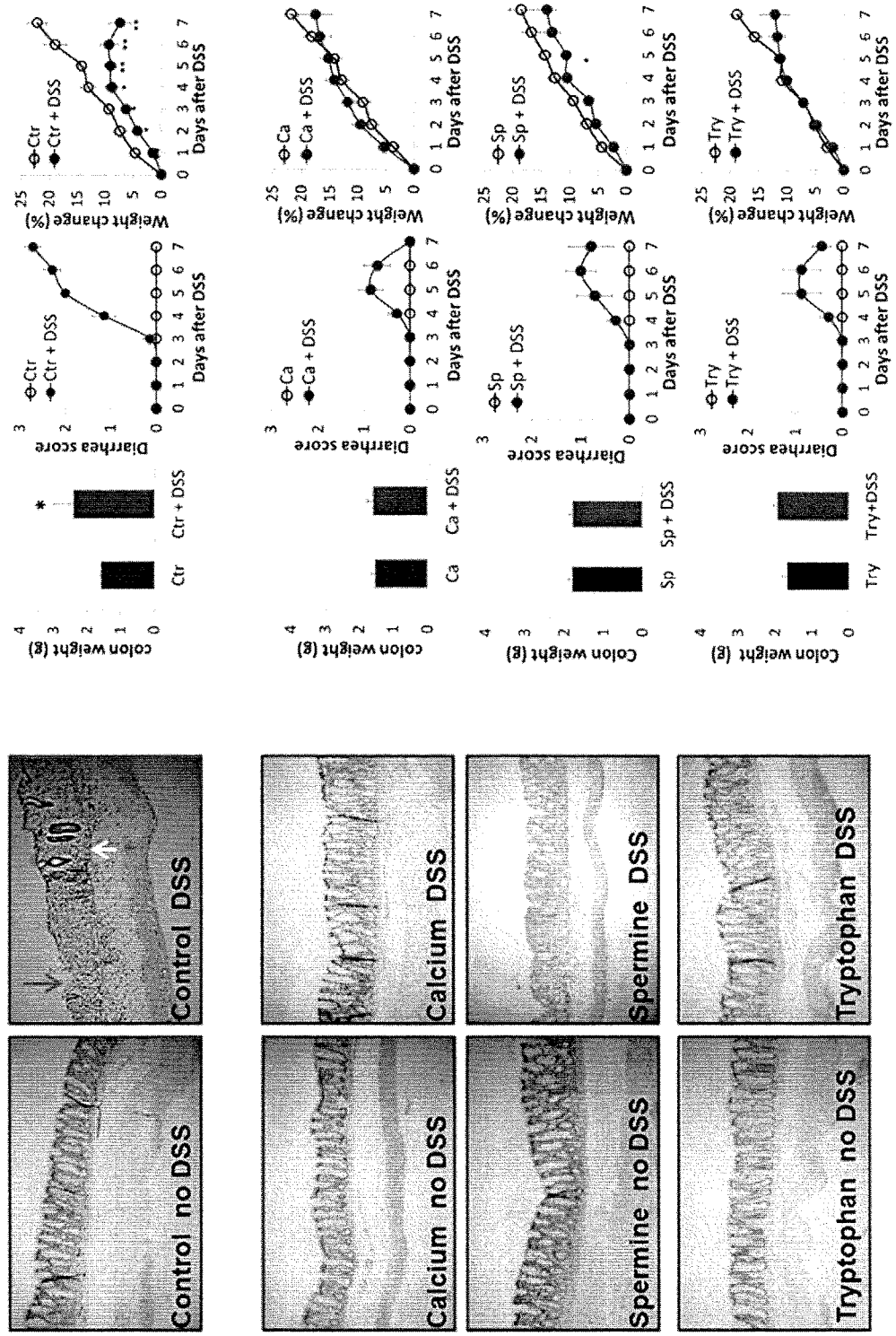
FIG. 4 shows that CaSR-activating nutrients ameliorate colitis in mice.
Figure 5:
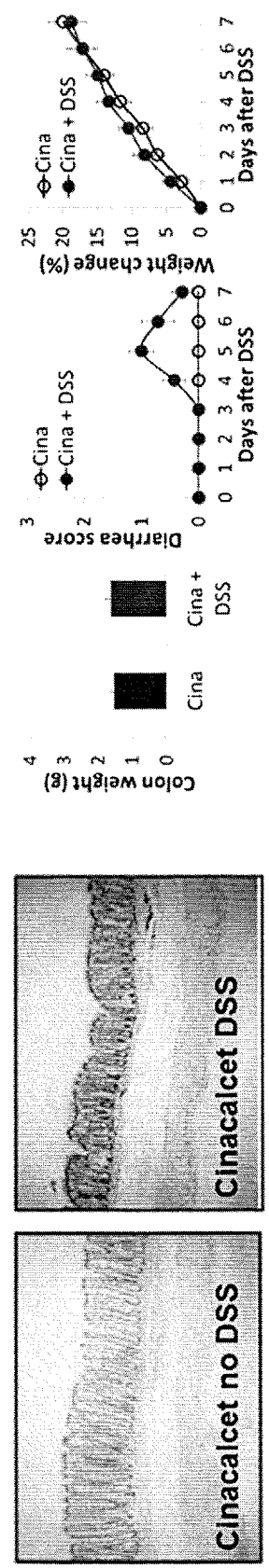
FIG. 5 shows that cinacalcet, a CaSR agonist, can be used to treat colitis.
Figure 6:
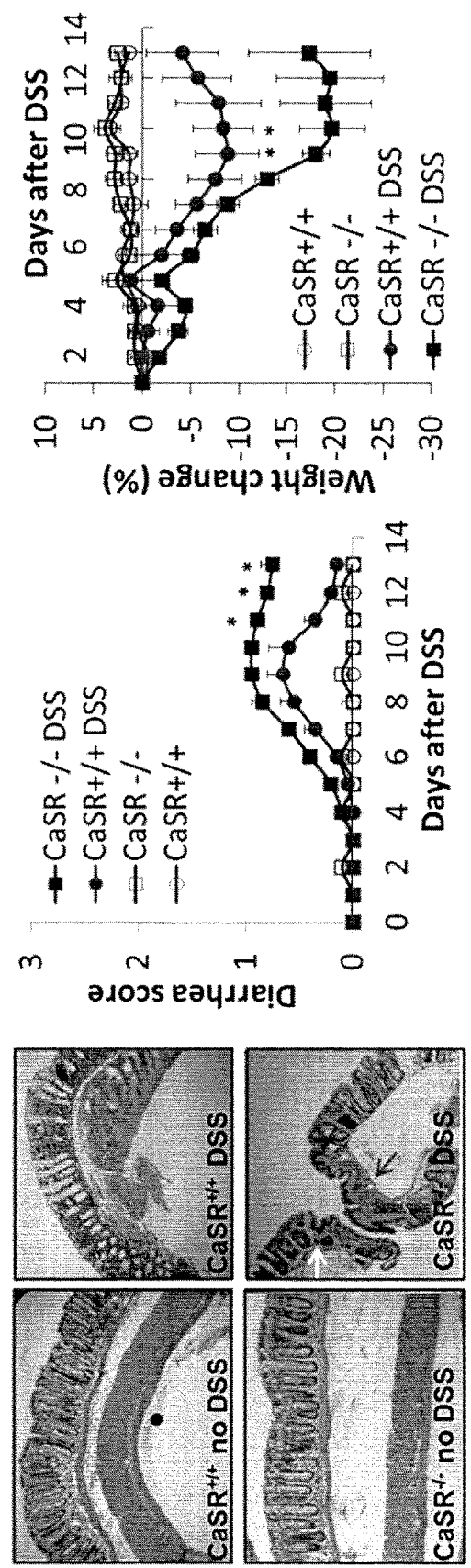
FIG. 6 shows that the loss of CaSR worsens dextran sulfate sodium (DSS)-induced colitis.
Figure 7:
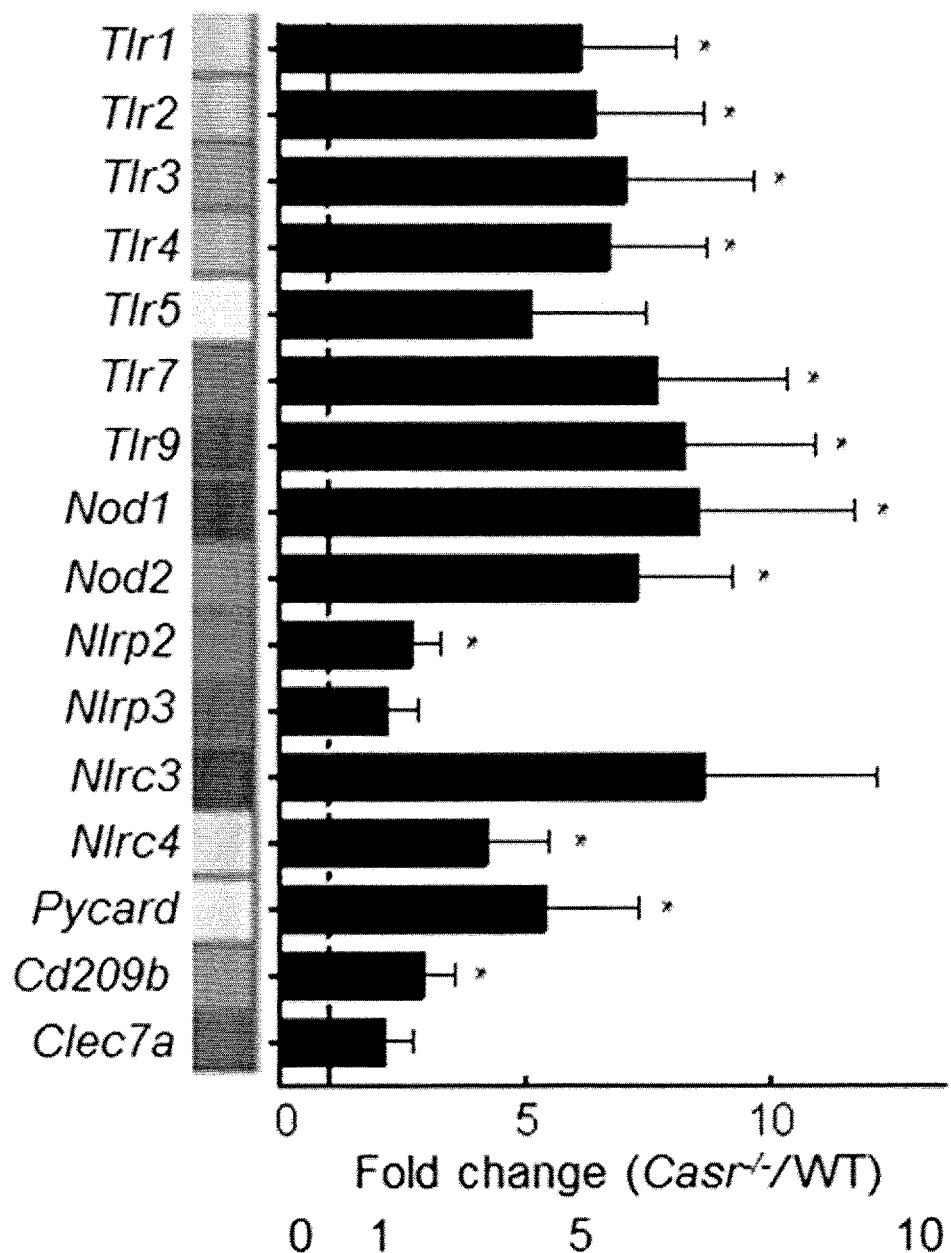
FIG. 7 shows that CaSR regulates the expression of PRRs.
Figure 8A:
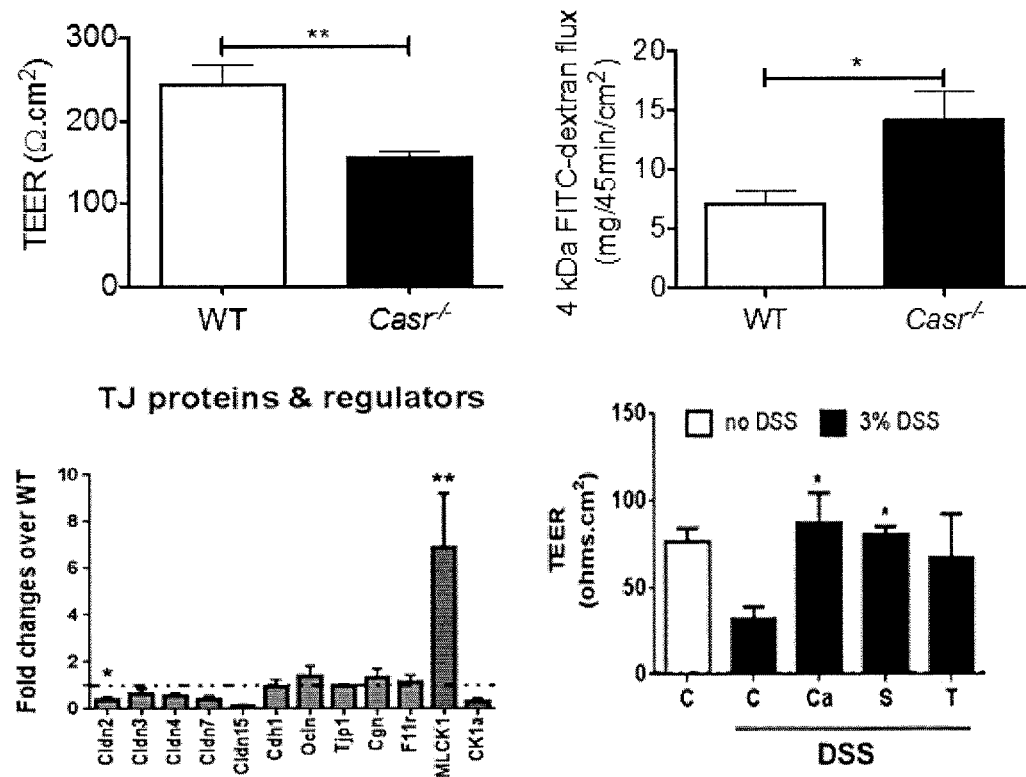
Figures 9A, 9B:
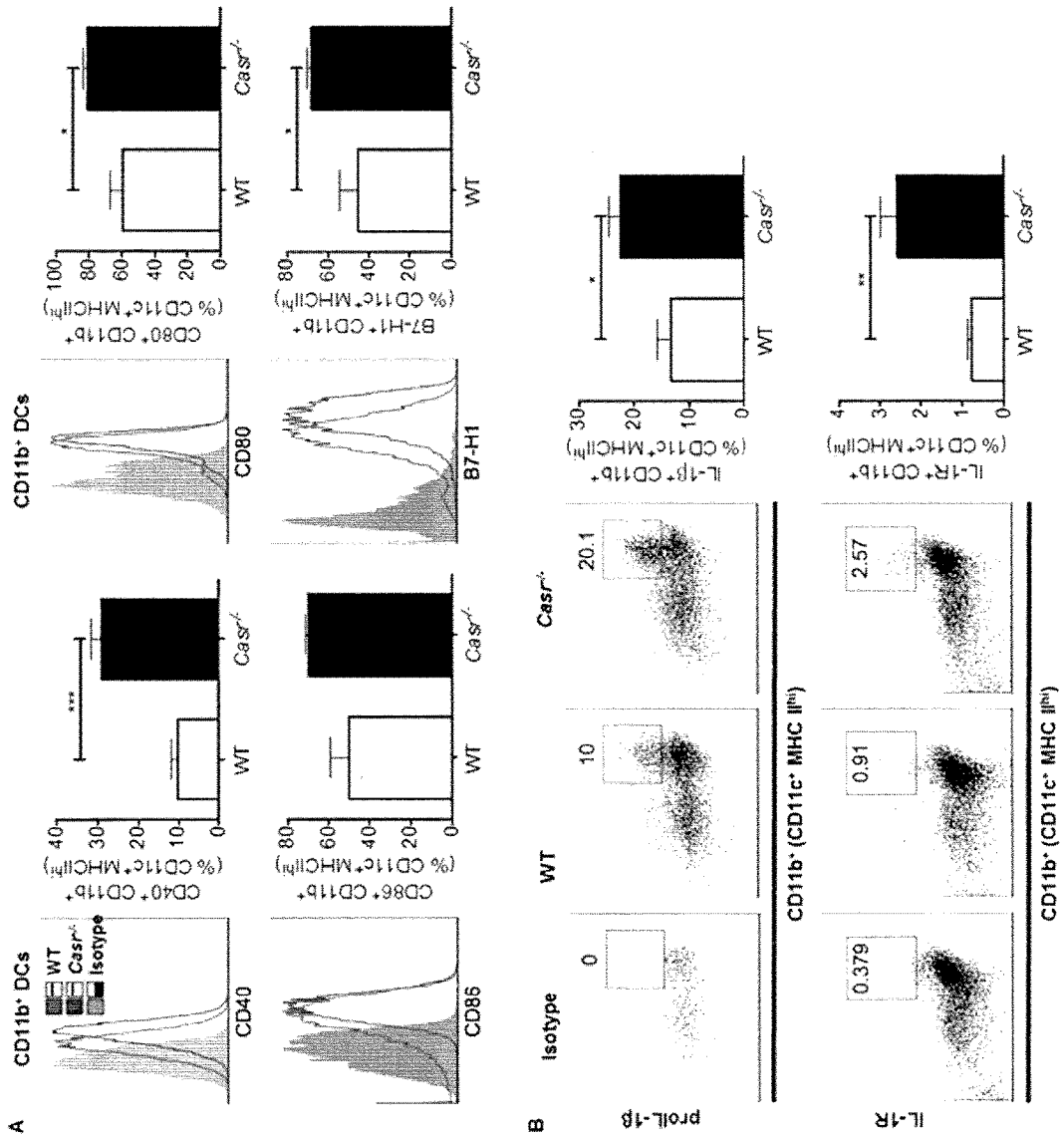
FIGS. 9A-9B show that the loss of CaSR leads to the activation of dendritic cells.
Figure 10:
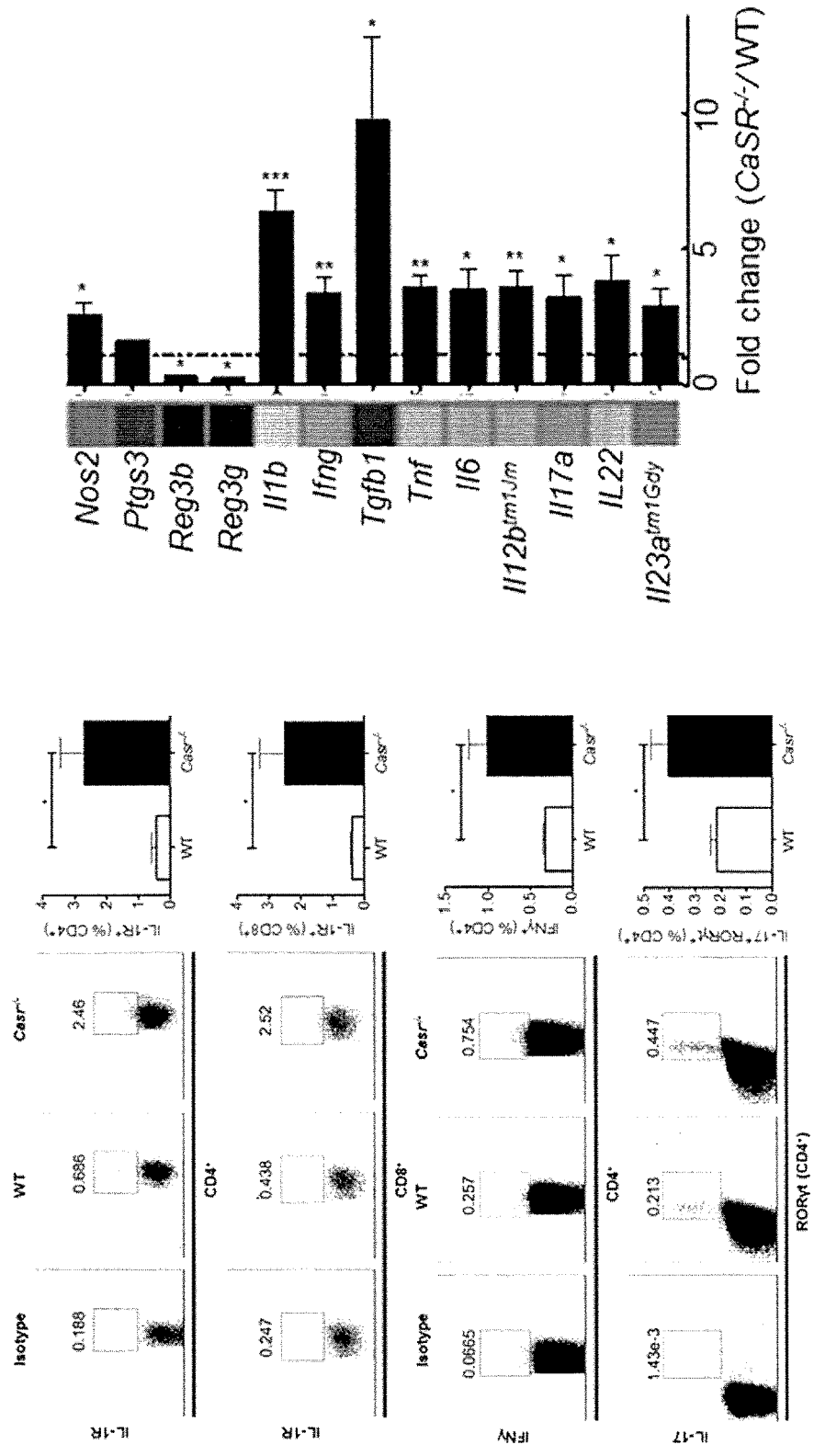
FIG. 10 shows that the elimination of CaSR signaling increases Th1/Th17 cells.
Figure 12A:
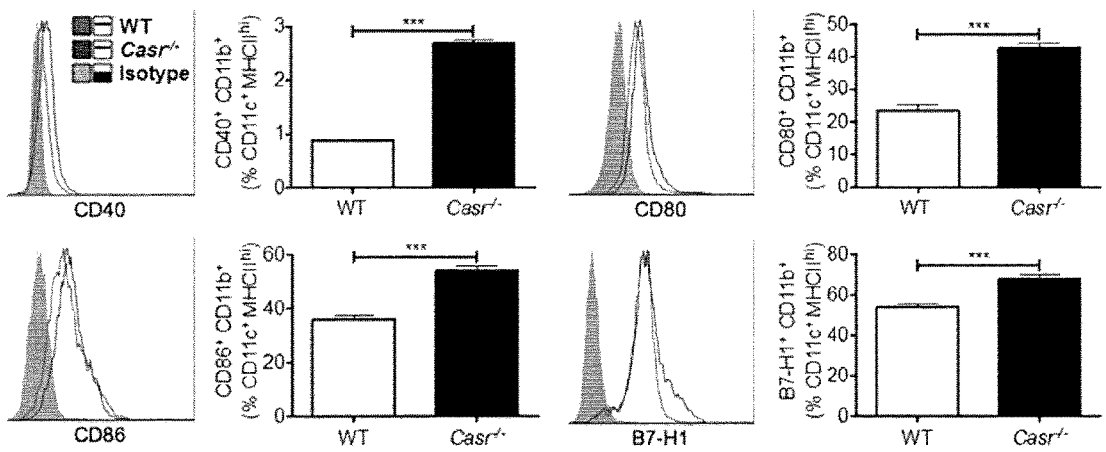
FIGS. 12A-12B show that defective CaSR signaling increases activated dendritic cells.
Figure 12B:
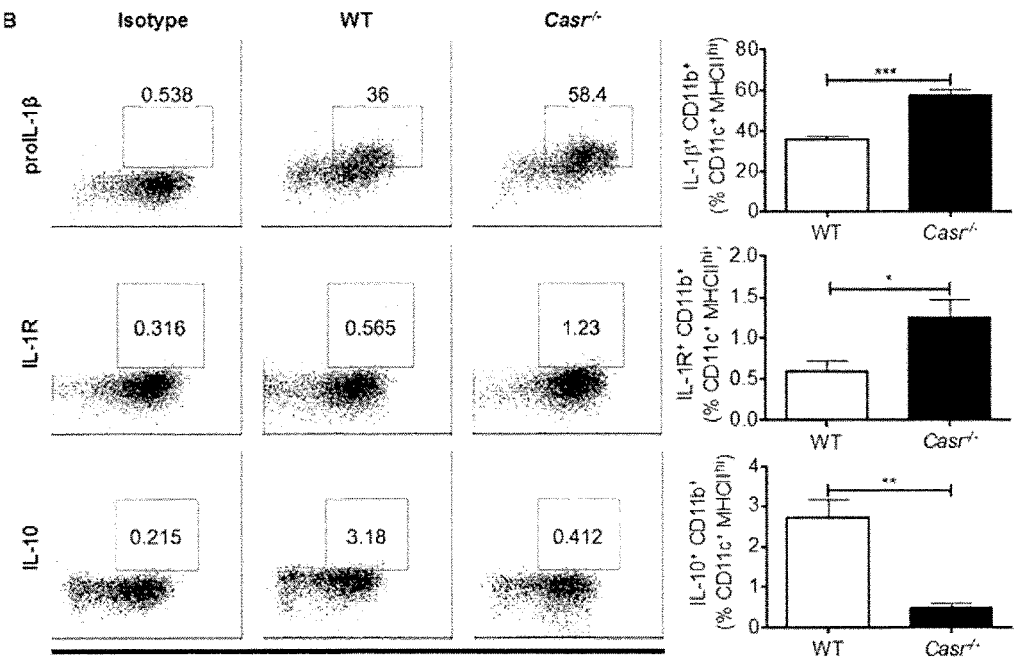
Figure 13:
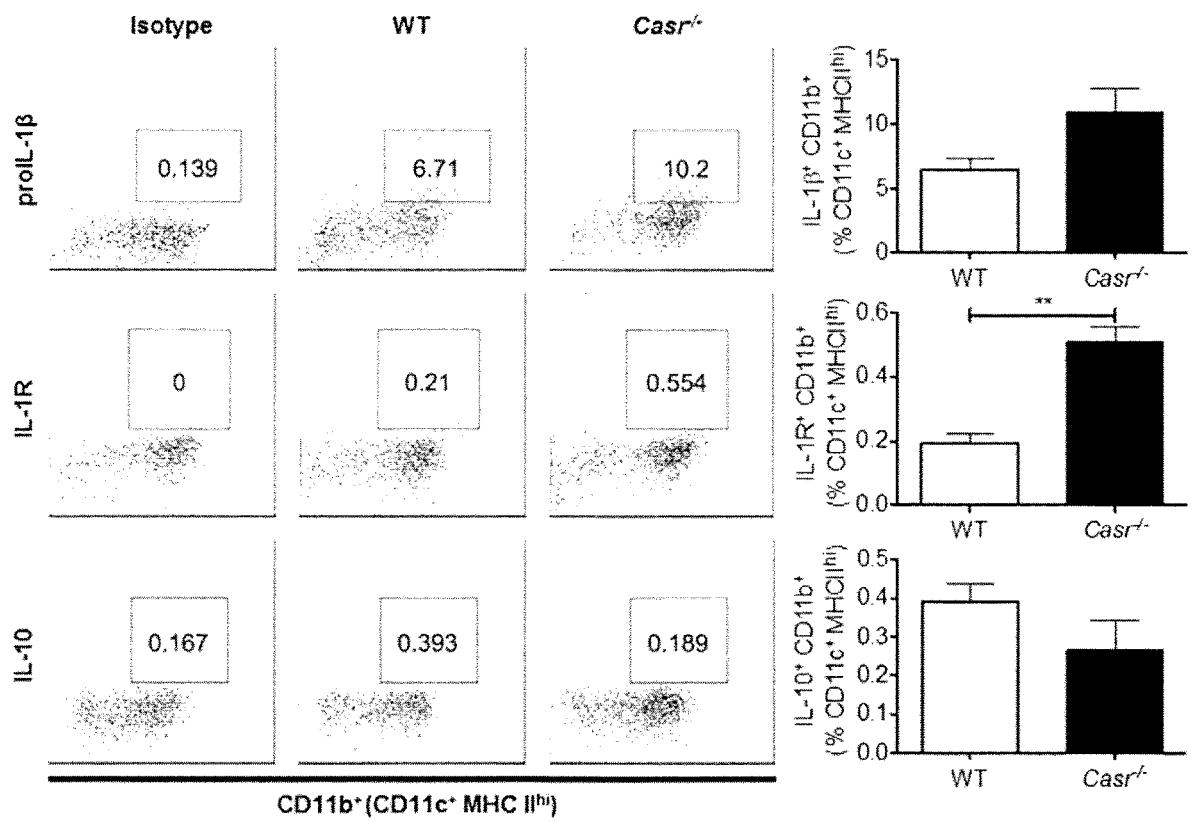
FIG. 13 shows that defective CaSR signaling increases activated dendritic cells.
Figure 16:
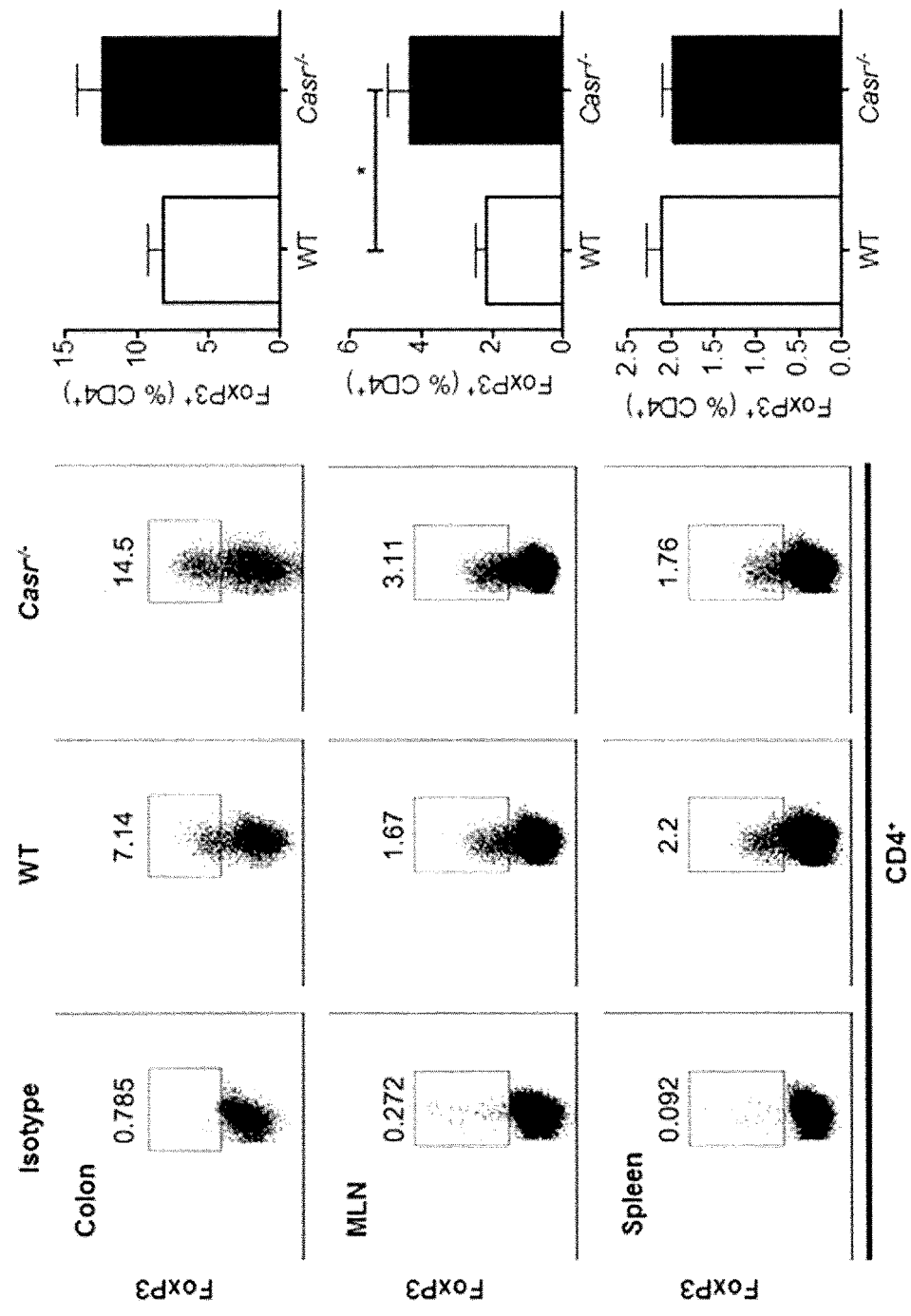
FIG. 16 shows that defective CaSR signaling leads to increased FoxP3 T (Treg) cells.
Figure 17:
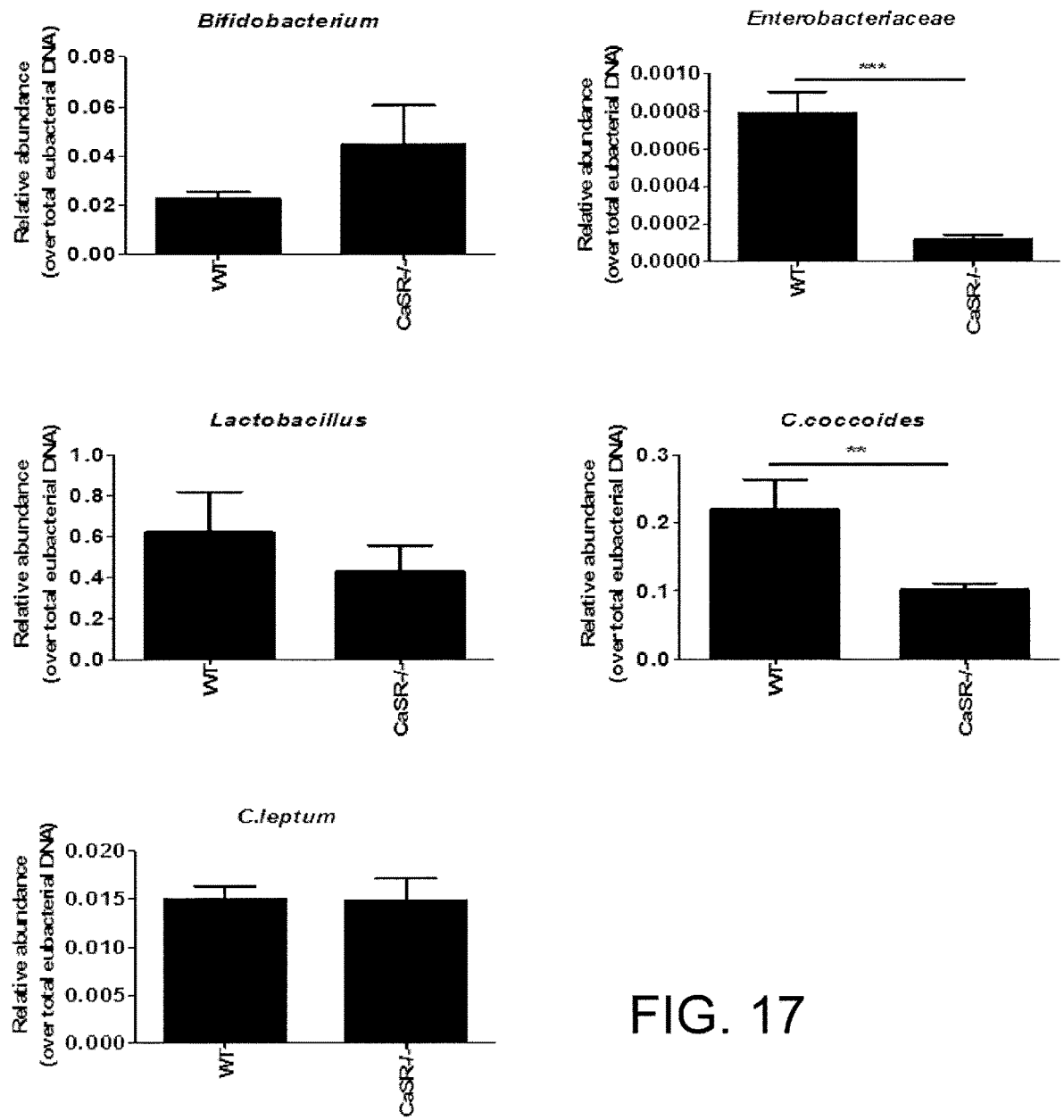
FIG. 17 shows that defective CaSR signaling results in a change in lumen microbial communities.
Figure 18:
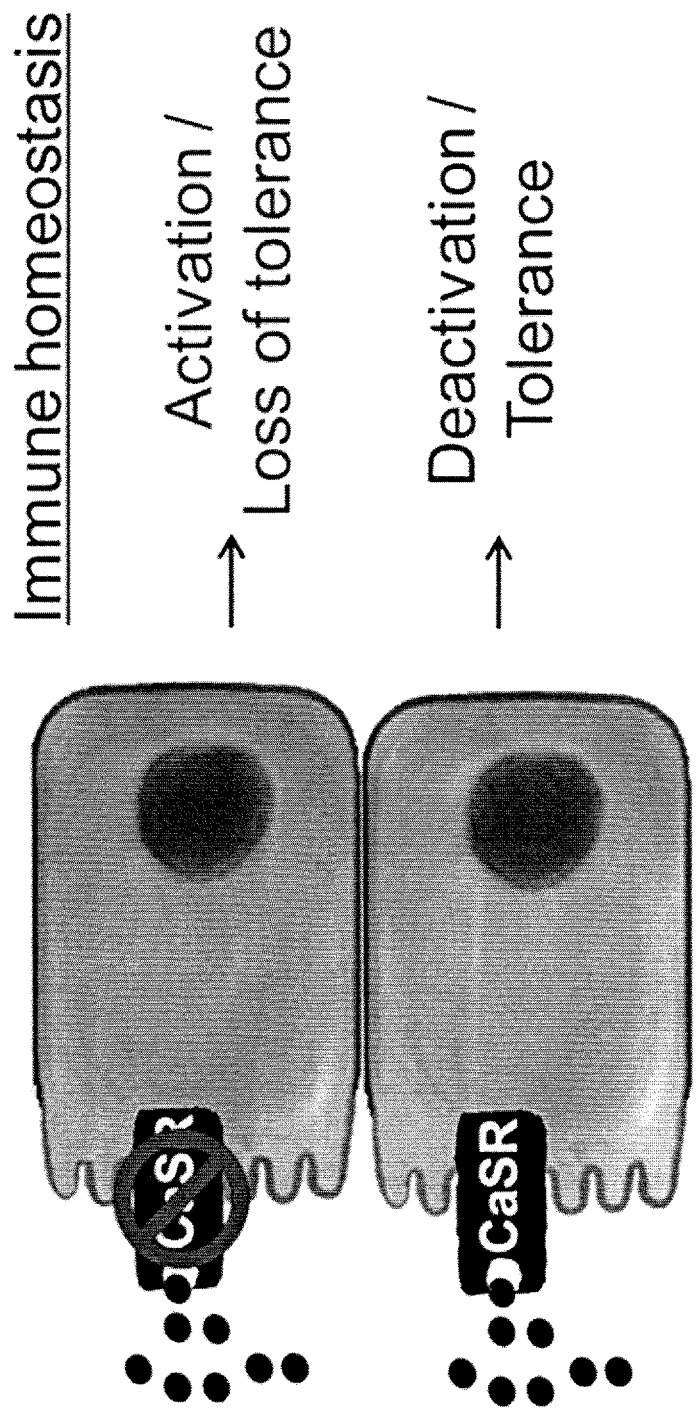
FIG. 18 shows that CaSR signaling is involved in intestinal immunity, and CaSR-activating nutrients can be used to enhance immune tolerance.

Briefly, three-to-six-week-old, pre-pubertal rats and mice (WT v. villin/cre-floxed CaSR) received antigens or CaSR-activating nutrients (calcium, spermine, tryptophan, and cinacalcet). After treatment, mice and rats were sacrificed, and epithelial barrier, cytokine expression, dendritic cell, T cell, and B cell activation, and response to inflammatory stress were determined (FIG. 2).

As shown in FIGS. 3-18, the administration of CaSR-activating nutrients in accordance with the current invention modulates immunity and can be used to treat inflammation in the gastrointestinal tract. CaSR-activating nutrients can be used to treat, or prevent the recurrence of, inflammatory bowel diseases, including Crohn's disease and colitis (such as ulcerative colitis).

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

I claim:

1. An anti-diarrheal composition consisting of calcium, potassium, magnesium, zinc, sodium, chloride, tryptophan; and, optionally, one or more ingredients selected from water; vitamins; preservatives; flavorings; bicarbonate; buffers; carbohydrates; citrate; butyrate; gluconate; acetic acid; the conjugate acids of citrate, gluconate and butyrate; and the conjugate base of acetic acid.

2. The composition, according to claim 1, which is a powder.

3. The composition, according to claim 1, comprising zinc gluconate.

\* \* \* \* \*

UNITED STATES PATENT AND TRADEMARK OFFICE
CERTIFICATE OF CORRECTION

PATENT NO. : 11,986,494 B2
APPLICATION NO. : 17/120883
DATED : May 21, 2024
INVENTOR(S) : Sam Xianjun Cheng It is certified that error appears in the above-identified patent and that said Letters Patent is hereby corrected as shown below:

In the Specification

Column 5,
Line 20, "65 rnM" should read --65 mM--
Line 32, "$HFO_4^{2-}$," should read --$HPO_4^{2-}$,--

Signed and Sealed this
Tenth Day of September, 2024

Katherine Kelly Vidal
Director of the United States Patent and Trademark Office